(12) United States Patent
Wu et al.

(10) Patent No.: US 9,388,370 B2
(45) Date of Patent: Jul. 12, 2016

(54) THERMOLYSIN-LIKE PROTEASE FOR CLEANING INSECT BODY STAINS

(75) Inventors: Songtao Wu, Ann Arbor, MI (US); Hongfei Jia, Ann Arbor, MI (US); Masahiko Ishii, Okazaki (JP); Minjuan Zhang, Ann Arbor, MI (US)

(73) Assignees: Toyota Motor Engineering & Manufacturing North America, Inc., Erlanger, KY (US); Toyota Motor Corporation, Toyota-shi (JP)

( * ) Notice: Subject to any disclaimer, the term of this patent is extended or adjusted under 35 U.S.C. 154(b) by 630 days.

(21) Appl. No.: 13/567,341

(22) Filed: Aug. 6, 2012

(65) Prior Publication Data

US 2012/0301946 A1 Nov. 29, 2012

Related U.S. Application Data

(63) Continuation-in-part of application No. 12/820,101, filed on Jun. 21, 2010, now Pat. No. 8,796,009.

(51) Int. Cl.
| | |
|---|---|
| *D06M 16/00* | (2006.01) |
| *C11D 3/386* | (2006.01) |
| *C11D 3/04* | (2006.01) |
| *C11D 3/20* | (2006.01) |
| *C11D 3/37* | (2006.01) |
| *C11D 7/04* | (2006.01) |
| *C11D 7/26* | (2006.01) |

(52) U.S. Cl.
CPC ............... *C11D 3/386* (2013.01); *C11D 3/044* (2013.01); *C11D 3/2003* (2013.01); *C11D 3/37* (2013.01); *C11D 3/38618* (2013.01); *C11D 7/04* (2013.01); *C11D 7/261* (2013.01)

(58) Field of Classification Search
CPC ...... C11D 3/386; C11D 3/044; C11D 3/2003; C11D 3/37; C11D 3/38618; C11D 7/04; C11D 7/261

See application file for complete search history.

(56) References Cited

U.S. PATENT DOCUMENTS

| | | | |
|---|---|---|---|
| 4,016,043 A | 4/1977 | Schuurs et al. | |
| 4,094,744 A | 6/1978 | Hartdegen et al. | |
| 4,098,645 A | 7/1978 | Hartdegen et al. | |
| 4,195,127 A | 3/1980 | Hartdegen et al. | |
| 4,195,129 A | 3/1980 | Fukui et al. | |
| 5,418,146 A | 5/1995 | Joo et al. | |
| 5,496,710 A * | 3/1996 | Nagao et al. | 435/68.1 |
| 5,559,163 A | 9/1996 | Dawson et al. | |
| 5,770,188 A | 6/1998 | Hamade et al. | |
| 5,914,367 A | 6/1999 | Dordick et al. | |
| 5,919,689 A | 7/1999 | Selvig et al. | |
| H1818 H | 11/1999 | Potgieter et al. | |
| 5,998,200 A | 12/1999 | Bonaventura et al. | |
| 6,030,933 A | 2/2000 | Herbots et al. | |
| 6,150,146 A | 11/2000 | Hamade et al. | |
| 6,291,582 B1 | 9/2001 | Dordick et al. | |
| 6,342,386 B1 | 1/2002 | Powers et al. | |
| 6,599,627 B2 | 7/2003 | Yeo et al. | |
| 6,855,746 B2 | 2/2005 | Yoshitake et al. | |
| 6,875,456 B2 | 4/2005 | Delest et al. | |
| 6,881,711 B1 | 4/2005 | Gershun et al. | |
| 6,905,733 B2 | 6/2005 | Russell et al. | |
| 7,335,400 B2 | 2/2008 | Russell et al. | |
| 7,632,793 B2 | 12/2009 | Lang | |
| 7,932,230 B2 | 4/2011 | McDaniel | |
| 7,939,500 B2 | 5/2011 | McDaniel | |
| 8,311,297 B2 | 11/2012 | Du et al. | |
| 8,388,904 B1 | 3/2013 | McDaniel et al. | |
| 8,394,618 B2 | 3/2013 | Buthe et al. | |
| 8,497,248 B2 | 7/2013 | McDaniel | |
| 8,618,066 B1 | 12/2013 | McDaniel | |
| 2004/0109853 A1 | 6/2004 | McDaniel | |
| 2004/0175407 A1 | 9/2004 | McDaniel | |
| 2004/0241497 A1 | 12/2004 | Sasaki et al. | |
| 2005/0049166 A1 | 3/2005 | Huang | |
| 2005/0079594 A1 * | 4/2005 | Marion | 435/196 |
| 2005/0147579 A1 | 7/2005 | Schneider et al. | |
| 2008/0038241 A1 | 2/2008 | Schasfoort et al. | |
| 2008/0108745 A1 | 5/2008 | Russell et al. | |
| 2008/0119381 A1 | 5/2008 | Wang et al. | |
| 2008/0319193 A1 * | 12/2008 | Grauert et al. | 544/258 |
| 2009/0045056 A1 | 2/2009 | Berberich et al. | |
| 2009/0238811 A1 | 9/2009 | McDaniel et al. | |
| 2010/0210745 A1 | 8/2010 | Mcdaniel et al. | |
| 2010/0248334 A1 | 9/2010 | McDaniel | |

(Continued)

FOREIGN PATENT DOCUMENTS

| | | |
|---|---|---|
| AU | 2003304222 A1 | 1/2005 |
| AU | 2004257205 A1 | 1/2005 |

(Continued)

OTHER PUBLICATIONS

Sookkheo et al. Protein Expression and Purification (2000) 20: 142-151.*
Translation for WO 01/53010 downloaded from https://patentscope.wipo.int Aug. 16, 2015.*
Transaltion for EP 2746378 downloaded from the EPO Aug. 16, 2015.*
Mansfeld, "The Stability of Engineered Thermostable Neutral Proteases from Bacillus Stearothermophilus in Organic Solvents and Detergents", Biotechnol. Bioeng. (2007) 97 (4): 672-679.
U.S. Appl. No. 12/243,666, filed Dec. 21, 2009.
U.S. Appl. No. 14/093,347, filed Nov. 29, 2013.
U.S. Appl. No. 14/097,128, filed Dec. 4, 2013.

(Continued)

*Primary Examiner* — Susan Hanley
(74) *Attorney, Agent, or Firm* — Dinsmore & Shohl LLP

(57) ABSTRACT

A substrate or coating is provided that includes a protease with enzymatic activity toward a component of a biological stain. Also provided is a process for facilitating the removal of a biological stain is provided wherein an inventive substrate or coating including a protease is capable of enzymatically degrading of one or more components of the biological stain to facilitate biological stain removal from the substrate or said coating.

12 Claims, 8 Drawing Sheets

(56) References Cited

U.S. PATENT DOCUMENTS

| | | |
|---|---|---|
| 2010/0269731 A1 | 10/2010 | Tofte Jespersen et al. |
| 2010/0279376 A1 | 11/2010 | Wang et al. |
| 2011/0076738 A1 | 3/2011 | Wang et al. |
| 2011/0240064 A1 | 10/2011 | Wales et al. |
| 2011/0250626 A1 | 10/2011 | Williams et al. |
| 2012/0097194 A1 | 4/2012 | McDaniel et al. |
| 2012/0238005 A1 | 9/2012 | Wieland et al. |
| 2013/0065291 A1 | 3/2013 | Jia et al. |
| 2013/0137159 A1 | 5/2013 | Buthe et al. |
| 2014/0193888 A1* | 7/2014 | Souter et al. .................. 435/263 |

FOREIGN PATENT DOCUMENTS

| | | |
|---|---|---|
| CA | 2538124 A1 | 12/2004 |
| EP | 609691 B1 | 5/1998 |
| EP | 1161502 B1 | 12/2004 |
| EP | 1551927 A1 | 7/2005 |
| EP | 1644452 A2 | 4/2006 |
| EP | 1660596 A1 | 5/2006 |
| EP | 2746378 A1 * | 6/2014 |
| FR | 2832145 A1 | 5/2003 |
| GB | 2410249 A | 7/2005 |
| GB | 2430436 A | 3/2007 |
| IL | 167413 A | 12/2010 |
| IL | 174122 A | 9/2011 |
| IL | 173658 A | 4/2012 |
| IL | 208769 A | 4/2012 |
| IL | 214668 A | 1/2013 |
| IL | 214669 A | 1/2013 |
| IL | 214670 A | 1/2013 |
| IL | 214671 A | 1/2013 |
| IL | 214672 A | 1/2013 |
| IL | 218129 A | 9/2013 |
| JP | 2002332739 A | 11/2002 |
| WO | 00/50521 A1 | 8/2000 |
| WO | WO 0153010 A1 * | 7/2001 |
| WO | 0216521 A1 | 2/2002 |
| WO | 2005/050521 A1 | 6/2005 |
| WO | 2009155115 A2 | 12/2009 |

OTHER PUBLICATIONS

Johanna Mansfeld et al.; Site-specific and random immobilization of thermolysin-like proteases reflected in the thermal inactivation kinetics; Biotechnol. Appl. Biochem. (2000); pp. 189-195.

Minoru Kumakura et al.; 201. Interaction of Enzyme with Polymer Matrix in Immobilized Enzymes; Helvetica Chimica Acta; vol. 66; Fasc. 7; (1983); pp. 2044-2048.

Jaroslava Turková; Immobilization of Enzymes on Hydroxyalkyl Methacrylate Gels; Immobilization Techniques; Methods in Enzymology; (1976); 344: pp. 66-83.

Masahiro Takagi et al.; Nucleotide Sequence and Promoter Region for the Neutral Protease Gene from Bacillus stearothermophilus; Journal of Bacteriology, Sep. 1985, pp. 824-831.

Kuniyo Inouye et al.; Engineering, expression, purification, and production of recombinant thermolysin; Biotechnology Annual Review; vol. 13; ISSN 1387-2656; pp. 43-64 (2007).

Novic, S. et al.; Protein-containing hydrophobic coatings and films, Biomaterials, 23: 441-448, 2002.

Drevon, G. et al.; High-Activity Enzyme-Polyurethane Coatings, Biotechnology and Bioengineering, 79(7): 785-794, Sep. 30, 2002.

* cited by examiner

SEQUENCE LISTING

```
<160> NUMBER OF SEQ ID NOS: 2

<210> SEQ ID NO 1
<211> LENGTH: 548
<212> TYPE: PRT
<213> ORGANISM: Geobacillus stearothermophilus

<400> SEQUENCE: 1

Met Asn Lys Arg Ala Met Leu Gly Ala Ile Gly Leu Ala Phe Gly Leu
1               5                   10                  15

Leu Ala Ala Pro Ile Gly Ala Ser Ala Lys Gly Glu Ser Ile Val Trp
                20                  25                  30

Asn Glu Gln Trp Lys Thr Pro Ser Phe Val Ser Gly Ser Leu Leu Asn
            35                  40                  45

Gly Gly Glu Gln Ala Leu Glu Leu Val Tyr Gln Tyr Val Asp Arg
    50                  55                  60

Glu Asn Gly Thr Phe Arg Leu Gly Gly Arg Ala Arg Asp Arg Leu Ala
65                  70                  75                  80

Leu Ile Gly Lys Gln Thr Asp Glu Leu Gly His Thr Val Met Arg Phe
                85                  90                  95

Glu Gln Arg His His Gly Ile Pro Val Tyr Gly Thr Met Leu Ala Ala
```

```
                100             105             110
His Val Lys Asp Gly Glu Leu Ile Ala Leu Ser Gly Ser Leu Ile Pro
            115                 120             125

Asn Leu Asp Gly Gln Pro Arg Leu Lys Lys Ala Lys Thr Val Thr Val
130                 135             140

Gln Gln Ala Glu Ala Ile Ala Glu Gln Asp Val Thr Glu Thr Val Thr
145             150                 155                         160

Lys Glu Arg Pro Thr Thr Glu Asn Gly Glu Arg Thr Arg Leu Val Ile
                    165                 170             175

Tyr Pro Thr Asp Gly Thr Ala Arg Leu Ala Tyr Glu Val Asn Val Arg
            180                 185             190

Phe Leu Thr Pro Val Pro Gly Asn Trp Val Tyr Ile Ile Asp Ala Thr
        195                 200             205

Asp Gly Ala Ile Leu Asn Lys Phe Asn Gln Ile Asp Ser Arg Gln Pro
    210                 215             220

Gly Gly Gly Gln Pro Val Ala Gly Ala Ser Thr Val Gly Val Gly Arg
225                 230             235                         240

Gly Val Leu Gly Asp Gln Lys Tyr Ile Asn Thr Thr Tyr Ser Ser Tyr
                245             250             255

Tyr Gly Tyr Tyr Tyr Leu Gln Asp Asn Thr Arg Gly Ser Gly Ile Phe
            260                 265             270

Thr Tyr Asp Gly Arg Asn Arg Thr Val Leu Pro Gly Ser Leu Trp Thr
        275                 280             285

Asp Gly Asp Asn Gln Phe Thr Ala Ser Tyr Asp Ala Ala Val Asp
    290                 295             300

Ala His Tyr Tyr Ala Gly Val Val Tyr Asp Tyr Tyr Lys Asn Val His
305             310             315                         320

Gly Arg Leu Ser Tyr Asp Gly Ser Asn Ala Ala Ile Arg Ser Thr Val
                325                 330             335

His Tyr Gly Arg Gly Tyr Asn Asn Ala Phe Trp Asn Gly Ser Gln Met
            340                 345             350

Val Tyr Gly Asp Gly Asp Gly Gln Thr Phe Leu Pro Phe Ser Gly Gly
                355             360             365

Ile Asp Val Val Gly His Glu Leu Thr His Ala Val Thr Asp Tyr Thr
370             375             380

Ala Gly Leu Val Tyr Gln Asn Glu Ser Gly Ala Ile Asn Glu Ala Met
385                 390             395                         400

Ser Asp Ile Phe Gly Thr Leu Val Glu Phe Tyr Ala Asn Arg Asn Pro
                405             410             415

Asp Trp Glu Ile Gly Glu Asp Ile Tyr Thr Pro Gly Val Ala Gly Asp
            420                 425             430

Ala Leu Arg Ser Met Ser Asp Pro Ala Lys Tyr Gly Asp Pro Asp His
                435             440             445

Tyr Ser Lys Arg Tyr Thr Gly Thr Gln Asp Asn Gly Gly Val His Thr
            450                 455             460

Asn Ser Gly Ile Ile Asn Lys Ala Ala Tyr Leu Leu Ser Gln Gly Gly
465                 470             475                         480

Val His Tyr Gly Val Ser Val Asn Gly Ile Gly Arg Asp Lys Met Gly
                485             490             495

Lys Ile Phe Tyr Arg Ala Leu Val Tyr Tyr Leu Thr Pro Thr Ser Asn
                500             505             510

Phe Ser Gln Leu Arg Ala Ala Cys Val Gln Ala Ala Asp Leu Tyr
            515                 520             525
```

Gly Ser Thr Ser Gln Glu Val Asn Ser Val Lys Gln Ala Phe Asn Ala
    530                 535                 540

Val Gly Val Tyr
545

<210> SEQ ID NO 2
<211> LENGTH: 1881
<212> TYPE: DNA
<213> ORGANISM: Geobacillus stearothermophilus

<400> SEQUENCE: 2

| | | | | | | |
|---|---|---|---|---|---|---|
| gatcaggaag | cattgcgcta | tggacgaagt | gagcctcctt | tcgttctcgg | gatatagccg | 60 |
| aaaagaacca | ggggaggaaa | aacgaaagtc | cgggccgtgc | acggagggcg | tgtcattgcc | 120 |
| gttcattttc | ccaatacaat | aaggatgact | attttggtaa | aattcagaat | gtgaggaatc | 180 |
| atcaaataca | tattcaagaa | aggggaagag | gagaatgaac | aaacgggcga | tgctcggggc | 240 |
| gatcgggctg | gcgttcggcc | tgctggcggc | gccgatcggc | gcttcggcga | aggggaatc | 300 |
| gatcgtctgg | aacgaacaat | ggaagacgcc | gtcattcgtg | tccggttcgt | tgctaaacgg | 360 |
| aggggaacaa | cgctggaag | agctcgttta | tcaatacgtc | gatcgggaaa | acggcacatt | 420 |
| ccgcctcggc | ggacgcgccc | gcgaccgttt | ggcgctgatc | ggcaaacaga | ctgacgaact | 480 |
| tggccatacc | gtgatgcggt | ttgaacagcg | gcatcacggt | ataccggttt | acggcaccat | 540 |
| gctggctgcc | catgtgaaag | atggcgagct | gatcgcgctg | tcggggtctt | taattcccaa | 600 |
| tttagacggc | cagccgcggt | tgaaaaaggc | gaaaacggtc | accgtccaac | aggcggaagc | 660 |
| tattgccgag | caagacgtaa | cggagacagt | gacgaaggag | cggccgacaa | ccgaaaacgg | 720 |
| cgagcggacg | cggctcgtca | tttacccgac | tgatggcacg | gcccgcctcg | cttatgaagt | 780 |
| gaacgtccgc | ttttttaacac | cggttcccgg | caactgggtg | tatatcattg | atgcaaccga | 840 |
| tggggccatt | ttgaataagt | tcaaccaaat | cgacagccgc | cagcccggcg | gcgggcagcc | 900 |
| ggtcgccggc | gcgtcgacgg | tcggcgtggg | ccggggtgtg | ttgggggatc | agaaatatat | 960 |
| caatacgacg | tattcctcgt | attacggcta | ctactatttg | caagacaata | cgcgcggcag | 1020 |
| cggcattttt | acgtatgacg | gacgaaaccg | caccgttttg | cccggcagct | tgtggaccga | 1080 |
| tgcgacaac | caatttaccg | ccagctatga | cgcggcggcc | gtggacgccc | attattacgc | 1140 |
| cggcgtcgtg | tatgattact | acaaaaatgt | gcacggccgg | ctgagctatg | acggcagcaa | 1200 |
| cgccgccatc | cgttcgaccg | tccattatgg | ccgcggctac | aacaacgcgt | tttggaacgg | 1260 |
| ttcgcaaatg | gtgtacggcg | atggcgacgg | acagacgttt | ttgccgtttt | ccggcggcat | 1320 |
| tgacgtcgtg | gggcatgagt | tgacccatgc | ggtgacggat | tatacggccg | ggcttgttta | 1380 |
| ccaaaacgaa | tctggcgcca | tcaatgaagc | gatgtccgat | attttcggca | cgctcgtgga | 1440 |
| gttctacgcc | aaccgcaacc | cggactggga | gattggcgaa | gacatttaca | cgcctggggt | 1500 |
| cgccggcgat | gcgctccgct | cgatgtccga | cccggcgaaa | tacggcgatc | cggatcatta | 1560 |
| ttccaaacgg | tacaccggca | cgcaagacaa | cggcggcgtc | catacaaaca | gcggcatcat | 1620 |
| caataaagcg | gcgtacttgc | tcagccaagg | cggcgtccat | tatggcgtga | gcgtcaacgg | 1680 |
| catcggccgc | gacaaaatgg | ggaaaatttt | ctaccgggcg | cttgtctact | atttgacgcc | 1740 |
| gacgtcgaac | ttcagccagc | tgcgtgccgc | ctgcgtgcaa | gcggccgctg | atttgtacgg | 1800 |
| gtcgacaagc | caagaagtca | actcggtgaa | acaggcgttc | aatgcggttg | gagtgtatta | 1860 |
| agacgatgag | gtcgtacgcg | t | | | | 1881 |

THERMOLYSIN-LIKE PROTEASE FOR CLEANING INSECT BODY STAINS

CROSS-REFERENCE TO RELATED APPLICATIONS

This application is a continuation-in-part of U.S. patent application Ser. No. 12/820,101, filed Jun. 21, 2010, the entire contents of which are incorporated herein by reference.

FIELD OF THE INVENTION

The present invention relates generally to coating compositions including bioactive substances and methods of their use to facilitate removal of insect stains. In specific embodiments, the invention relates to compositions and methods for prevention of insect stain adherence to a surface as well as insect stain removal by incorporating a protease into or on polymer composite materials to degrade insect body components.

BACKGROUND OF THE INVENTION

Many outdoor surfaces are subject to stain or insult from natural sources such as bird droppings, resins, and insect bodies. As a result, the resulting stain often leaves unpleasant marks on the surface deteriorating the appearance of the products.

Traditional self-cleaning coatings and surface are typically based on water rolling or sheeting to carry away inorganic materials. These show some level of effectiveness for removal of inorganic dirt, but are less effective for cleaning stains from biological sources, which consist of various types of organic polymers, fats, oils, and proteins each of which can deeply diffuse into the subsurface of coatings. Prior art approaches aim to reduce the deposition of stains on a surface and facilitate its removal capitalize on the "lotus-effect" where hydrophobic, oleophobic and super-amphiphobic properties are conferred to the surface by polymeric coatings containing appropriate nanocomposites. An exemplary coating contains fluorine and silicon nanocomposites with good roll off properties and very high water and oil contact angles. When used on rough surfaces like sandblasted glass, nanocoatings may act as a filler to provide stain resistance. A drawback of these "passive" technologies is that they are not optimal for use in high gloss surfaces because the lotus-effect is based on surface roughness.

Photocatalytic coatings are promising for promoting self-cleaning of organic stains. Upon the irradiation of sun light, a photocatalyst such as $TiO_2$ chemically breaks down organic dirt that is then washed away by the water sheet formed on the super hydrophilic surface. As an example, the photocatalyst $TiO_2$ was used to promote active fingerprint decomposition of fingerprint stains in U.S. Pat. Appl. Publ. 2009/104086. A major drawback to this technology is its limitation to use on inorganic surfaces due to the oxidative impairment of the polymer coating by $TiO_2$. Also, this technology is less than optimal for automotive coatings due to a compatibility issue: $TiO_2$ not only decomposes dirt, but also oxidizes polymer resins in the paint.

Therefore, there is a need for new materials or coatings that can actively promote the removal of biological stains on surfaces or in coatings and minimize the requirement for maintenance cleaning.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A process of facilitating the removal of biological stains is provided including providing a liquid bioactive coating with an associated thermolysin-like protease such that said protease is capable of enzymatically degrading a component of a biological stain. A thermolysin-like protease is optionally a member of the M4 thermolysin-like proteases which include thermolysin or analogues thereof. In some embodiments a protease is a bacterial neutral thermolysin-like-protease from *Bacillus stearothermophilus* or an analogue thereof.

Also provided is a composition for facilitating biological stain removal including a liquid coating material and a thermolysin capable of degrading a biological stain component, wherein the thermolysin is associated with the coating. The thermolysin-like protease is optionally a bacterial neutral thermolysin from *Bacillus stearothermophilus*.

DETAILED DESCRIPTION OF THE PREFERRED EMBODIMENTS

Figure 1:
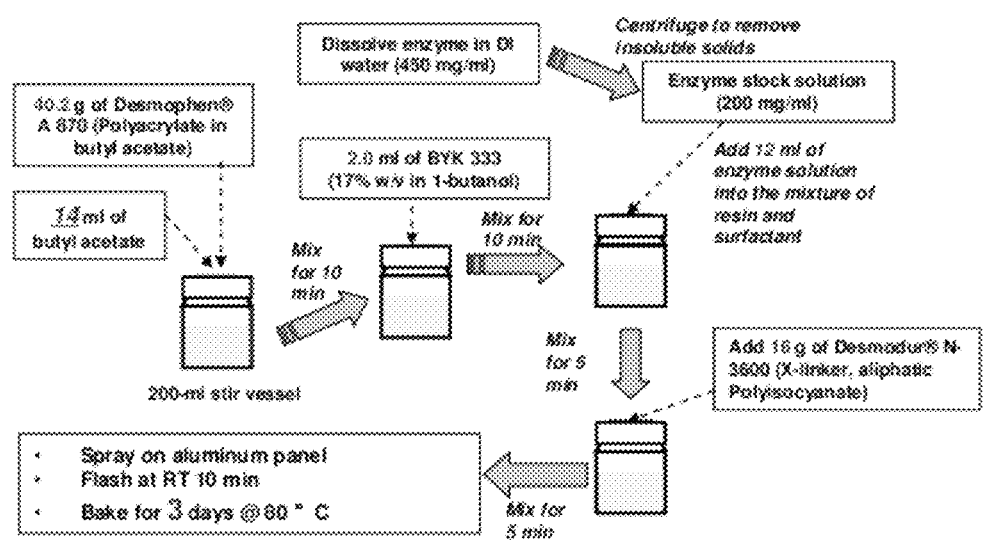
FIG. 1 represents a schematic of a spray-down application process of one embodiment of a coating.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While processes are described as an order of individual steps or using specific materials, it is appreciated that described steps or materials may be interchangeable such that the description of the invention includes multiple parts or steps arranged in many ways as is readily appreciated by one of skill in the art.

The present invention is based on the catalytic activity of a protease enzyme to selectively degrade components of organic stains thus, promoting active stain removal. Organic stains typically include organic polymers, fats, oils, and proteins. It was traditionally difficult to identify a protease that was simultaneously incorporatable into or on a coating or substrate with remaining activity and successfully promote active breakdown and subsequent removal of biological stains, particularly stains from insect sources. The inventors unexpectedly discovered that a particular family of hydrolases, the bacterial thermolysins (EC 3.4.24.27), particularly the active extracellular fragment of enzyme *G. stearothermophilus* TLP (extracellular Sterolysin) at an activity in excess of 20,000 U/g when in a coating material successfully promoted biological stain removal whereas similar proteases, even other closely related metalloproteases, were unsuccessful.

The protease is either immobilized into or on coatings or substrates, or is a component of a fluid (forming a bioactive liquid coating) used to temporarily contact and coat a surface, and catalyzes the degradation of biological stain components into smaller molecules. The small product molecules are less strongly adherent to a surface or coating incorporating a protease, or is more easily removed with a liquid coating including a protease, such that gentle rinsing, optionally with water, air, or other fluid, promotes removal of the biological material from the surface or coating. Thus, the invention has utility as a composition and method for the active removal of biological stains from surfaces.

It is appreciated that the while the description herein is directed to coatings, the materials described herein may also be substrates or articles that do not require a coating thereon for promotion of functional biological stain removal. As such, the word "coating" as used herein means a material that is operable for layering on a surface of one or more substrates, or may comprise the substrate material itself. In some embodiments a coating is a temporary coating or is otherwise a material designed to be applied as a rinsing or cleaning agent such as a windshield washer fluid. As such, the methods and compositions disclosed herein are generally referred to as a protease associated with a coating for exemplary purposes only. One of ordinary skill in the art appreciates that the description is equally applicable to substrates themselves.

An inventive method includes providing a coating with a protease such that the protease is enzymatically active and capable for degrading one or more components of a biological stain that is applied prior to or after the coating is associated with a substrate. In particular embodiments a biological stain is based on bioorganic matter such as that derived from an insect, optionally an insect body.

A biological stain as defined herein is a bioorganic stain, mark, or residue left behind after an organism contacts a substrate or coating. A biological stain is not limited to marks or residue left behind after a coating is contacted by an insect body. Other sources of bioorganic stains are illustratively: insect wings, legs, or other appendages; bird droppings; fingerprints or residue left behind after a coating is contacted by an organism; or other sources of biological stains.

A protease is optionally a bacterial metalloprotease such as a member of the M4 family of bacterial thermolysin-like proteases of which thermolysin is the prototype protease (EC 3.4.24.27) or analogues thereof. A protease is optionally the bacterial neutral thermolysin-like-protease (TLP) derived from *Geobacillus stearothermophilus* (*Bacillus thermoproteolyticus* Var. *Rokko*) (illustratively sold under the trade name "Thermoase C160" available from Amano Enzyme U.S.A., Co. (Elgin, Ill.)), with a sequence of residues 230-548 of SEQ ID NO: 1, or analogues thereof. A protease is optionally any protease presented in de Kreig, et al., *J Biol Chem*, 2000; 275(40):31115-20, or Takagi, M, et al., *J Bacteriol*, 1985; 163:824-831, the contents of each of which are incorporated herein by reference. Illustrative examples of a protease include the thermolysin-like-proteases from *Bacillis cereus* (Accession No. P05806), *Lactobacillis* sp. (Accession No. Q48857), *Bacillis megaterium* (Accession No. Q00891), *Bacillis* sp. (Accession No. Q59223), *Alicyclobacillis acidocaldarious* (Accession No. Q43880), *Bacillis caldolyticus* (Accession NO. P23384), *Bacillis thermoproteolyticus* (Accession No. P00800), *Bacillus stearothermophilus* (Accession No. P43133), *Geobacillus stearothermophilus* (P06874), *Bacillus subtilis* (Accession No. P06142), *Bacillus amyloliquefaciens* (Accession No. P06832), *Lysteria monocytogenes* (Accession No: P34025; P23224), or active fragments of each, among others known in the art. In particular embodiments, a TLP is the active fragment of *Geobacillus stearothermophilus* Stearolysin (P06874) encompassing residues 230 to 548, or an active analogue thereof. The sequences at each accession number listed herein are incorporated herein by reference. Methods of cloning, expressing, and purifying any protease operable herein is achievable by methods ordinarily practiced in the art illustratively by methods disclosed in Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002, the contents of each of which are incorporated herein by reference.

An analogue of a protease is optionally a fragment of a protease or includes one or more non-wild-type amino acids in the peptide sequence. An analogue of a protease is a polypeptide that has some level of activity toward a natural or synthetic substrate of a protease. An analogue optionally has between 0.1% and 200% the activity of a wild-type protease. The term "protease" as used herein includes analogues in some embodiments. In some embodiments, the term "protease" is exclusive of an analogue of a wild-type protease.

Specific examples of proteases illustratively have 10,000 U/g protease activity or more wherein one (1) U (unit) is defined as the amount the enzyme that will liberate the non-proteinous digestion product from milk casein (final concentration 0.5%) to give Folin's color equivalent to 1 µmol of tyrosine per minute at the reaction initial reaction stage when a reaction is performed at 37° C. and pH 7.2. Illustratively, the protease activity is anywhere between 10,000 PU/g to 1,500,000 U/g or any value or range therebetween, or greater. It is appreciated that lower protease activities are operable in some embodiments. Protease activity is optionally in excess of 20,000 U/g. Optionally, protease activity is between 300,000 U/g and 2,000,000 U/g in buffer, or any value or range therebetween, or higher.

A protease is a "peptide," "polypeptide," and "protein" (terms used herein synonymously) and is intended to mean a natural or synthetic compound containing two or more amino acids having some level of activity toward a natural or synthetic substrate of a wild-type protease. A wild-type protease is a protease that has an amino acid sequence identical to that found in an organism in nature. An illustrative example of a wild-type protease is that found at GenBank Accession No. P06874 and SEQ ID NO: 1.

A protease may function with one or more cofactor ions or proteins. A cofactor ion is illustratively a zinc, cobalt, or calcium.

Methods of screening for protease activity are known and standard in the art. Illustratively, screening for protease activity in a protease illustratively includes contacting a protease with a natural or synthetic substrate of a protease and measuring the enzymatic cleavage of the substrate. Illustrative substrates for this purpose include casein of which is cleaved by a protease to liberate folin-positive amino acids and peptides (calculated as tyrosine) that are readily measured by techniques known in the art. The synthetic substrate furylacryloylated tripeptide 3-(2-furylacryloyl)-L-glycyl-L-leucine-L-alanine obtained from Bachem AG, Bubendorf, Switzerland is similarly operable.

Amino acids present in a protease include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine; as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxylsoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. A lipase includes peptides having between 2 and about 1000 amino acids or having a molecular weight in the range of about 150-350,000 Daltons.

A protease is obtained by any of various methods known in the art illustratively including isolation from a cell or organism, chemical synthesis, expression of a nucleic acid sequence, and partial hydrolysis of proteins. Chemical methods of peptide synthesis are known in the art and include solid phase peptide synthesis and solution phase peptide synthesis or by the method of Hackeng, T M, et al., *Proc Natl Acad Sci USA*, 1997; 94(15):7845-50, the contents of which are incorporated herein by reference. A protease may be a naturally occurring or non-naturally occurring protein. The term "naturally occurring" refers to a protein endogenous to a cell, tissue or organism and includes allelic variations. A non-naturally occurring peptide is synthetic or produced apart from its naturally associated organism or modified and is not found in an unmodified cell, tissue or organism.

Modifications and changes can be made in the structure of a protease and still obtain a molecule having similar characteristics as wild-type protease (e.g., a conservative amino acid substitution). For example, certain amino acids can be substituted for other amino acids in a sequence without appreciable loss of activity or optionally to reduce or increase the activity of an unmodified protease. Because it is the interactive capacity and nature of a polypeptide that defines that polypeptide's biological functional activity, certain amino acid sequence substitutions can be made in a polypeptide sequence and nevertheless obtain a polypeptide with like or other desired properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution using amino acids whose hydropathic indices are within ±2, those within ±1, and those within ±0.5 are optionally used.

Substitution of like amino acids can also be made on the basis of hydrophilicity. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain an enzymatically equivalent polypeptide. In such changes, the substitution of amino acids whose hydrophilicity values are within ±2, those within ±1, and those within ±0.5 are optionally used.

Amino acid substitutions are optionally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include analogues having about 50%, 60%, 70%, 80%, 90%, 95%, or 99% sequence identity to a wild-type protease.

It is further appreciated that the above characteristics are optionally taken into account when producing a protease with reduced or improved enzymatic activity. Illustratively, substitutions in a substrate binding site, exosite, cofactor binding site, catalytic site, or other site in a protease protein may alter the activity of the enzyme toward a substrate. In considering such substitutions the sequences of other known naturally occurring or non-naturally occurring proteases may be taken into account. Illustratively, a corresponding mutation to that of Asp213 in thermolysin is operable such as that done by Miki, Y, et al., Journal of Molecular Catalysis B: Enzymatic, 1996; 1:191-199, the contents of which are incorporated herein by reference. Optionally, a substitution in thermolysin of L144 such as to serine alone or along with substitutions of G8C/N60C/S65P are operable to increase the catalytic efficiency by 5-10 fold over the wild-type enzyme. Yasukawa, K, and Inouye, K, Biochimica et Biophysica Acta (BBA)—Proteins & Proteomics, 2007; 1774:1281-1288, the contents of which are incorporated herein by reference. The mutations in the bacterial neutral protease from Bacillus stearothermophilus of N116D, Q119R, D150E, and Q225R as well as other mutations similarly increase catalytic activity. De Kreig, A, et al., J. Biol. Chem., 2002; 277:15432-15438, the contents of which are incorporated herein by reference. De Kreig also teach several substitutions including multiple substitutions that either increase or decrease the catalytic activity of the protease. Id. and De Kreig, Eur J Biochem, 2001; 268(18): 4985-4991, the contents of which are incorporated herein by reference. Other substitutions at these or other sites optionally similarly affect enzymatic activity. It is within the level of skill in the art and routine practice to undertake site directed mutagenesis and screen for subsequent protein activity such as by the methods of De Kreig, Eur J Biochem, 2001; 268 (18):4985-4991 for which this reference is similarly incorporated herein by reference.

A protease is illustratively recombinant. Methods of cloning, synthesizing or otherwise obtaining nucleic acid sequences encoding a protease are known and standard in the art that are equally applicable to lipase. Similarly, methods of cell transfection and protein expression are similarly known in the art and are applicable herein. Exemplary cDNA encoding the protein sequence of SEQ ID NO: 1 is the nucleotide sequence found at accession number M11446 and SEQ ID NO: 2.

A protease may be coexpressed with associated tags, modifications, other proteins such as in a fusion peptide, or other modifications or combinations recognized in the art. Illustrative tags include 6×His, FLAG, biotin, ubiquitin, SUMO, or other tag known in the art. A tag is illustratively cleavable such as by linking to lipase or an associated protein via an enzyme cleavage sequence that is cleavable by an enzyme known in the art illustratively including Factor Xa, thrombin, SUMOstar protein as obtainable from Lifesensors, Inc., Malvern, Pa., or trypsin. It is further appreciated that chemical cleavage is similarly operable with an appropriate cleavable linker.

Protein expression is illustratively accomplished from transcription of a protease nucleic acid sequence, illustratively that of SEQ ID NO: 2, translation of RNA transcribed from the protease nucleic acid sequence or analogues thereof. An analog of a nucleic acid sequence is any sequence that when translated to protein will produce a protease analogue. Protein expression is optionally performed in a cell based system such as in E. coli, Hela cells, or Chinese hamster ovary cells. It is appreciated that cell-free expression systems are similarly operable.

It is recognized that numerous analogues of protease are operable and within the scope of the present invention including amino acid substitutions, alterations, modifications, or other amino acid changes that increase, decrease, or not alter the function of the protease protein sequence. Several post-translational modifications are similarly envisioned as within the scope of the present invention illustratively including incorporation of a non-naturally occurring amino acid, phosphorylation, glycosylation, addition of pendent groups such as biotinylation, fluorophores, lumiphores, radioactive groups, antigens, or other molecules.

An inventive method uses an inventive composition that is one or more proteases incorporated into a substrate itself or into a coating, optionally for application on a substrate. The protease enzyme is optionally non-covalently associated and/or covalently attached to the substrate or coating material or is otherwise associated therewith such as by bonding to the surface or by intermixing with the substrate/coating material during manufacture such as to produce entrapped protease. In some embodiments the protease is covalently attached to the substrate or coating material either by direct covalent interaction between the protease and one or more components of the substrate or coating material or by association via a link moiety such as that described in U.S. Pat. App. Publ. No.

2008/0119381, the contents of which are incorporated herein by reference. In some embodiments, such as in coatings useful as cleaning agents, illustratively, windshield washing solutions, a protease is in solution or suspension within the coating solution.

There are several ways to associate protease with a substrate or coating. One of which involves the application of covalent bonds. Specifically, free amine groups of the protease may be covalently bound to an active group of the substrate. Such active groups include alcohol, thiol, aldehyde, carboxylic acid, anhydride, epoxy, ester, or any combination thereof. This method of incorporating protease delivers unique advantages. First, the covalent bonds tether the proteases permanently to the substrate and thus place them as an integral part of the final composition with much less, if any at all, leakage of the protease. Second, the covalent bonds provide extended enzyme lifetime. Over time, proteins typically lose activity because of the unfolding of their polypeptide chains. Chemical bonding such as covalent bonding effectively restricts such unfolding, and thus improves the protein life. The life of a protein is typically determined by comparing the amount of activity reduction of a protein that is free or being physically adsorbed with that of a protein covalently-immobilized over a period of time.

Proteases are optionally uniformly dispersed throughout the substrate or coating network to create a substantially homogenous protein platform. In so doing, proteases may be first modified with polymerizable groups. The modified proteases may be solubilized into organic solvents, optionally, in the presence of surfactant, and thus engage the subsequent polymerization with monomers such as methyl methacrylate (MMA) or styrene in the organic solution. The resulting composition optionally includes protease molecules homogeneously dispersed throughout the network.

Proteases are optionally attached to surfaces of a substrate. An attachment of proteases corresponding to approximately 100% surface coverage was achieved with polystyrene particles with diameters range from 100 to 1000 nm.

Chemical methods of protease attachment to materials will naturally vary depending on the functional groups present in the protease and in the material components. Many such methods exist. For example, methods of attaching proteins (such as enzymes) to other substances are described in O'Sullivan et al, *Methods in Enzymology*, 1981; 73:147-166 and Erlanger, *Methods in Enzymology*, 1980; 70:85-104, each of which are herein incorporated by reference.

Proteases are optionally present in a coating that is layered upon a substrate wherein the protease is optionally entrapped in the coating material, admixed therewith, modified and integrated into the coating material or layered upon a coating similar to the mechanisms described for interactions between a protease and substrate material.

Materials operable for interactions with a protease to form an active substrate or coating illustratively include organic polymeric materials. The combination of these materials and a protease form a protein-polymer composite material that is used as a substrate material or a coating.

Methods of preparing protein-polymer composite materials illustratively include use of aqueous solutions of protease and non-aqueous organic solvent-borne polymers to produce bioactive organic solvent-borne protein-polymer composite materials.

Methods of preparing protein-polymer composite materials are illustratively characterized by dispersion of protease in solvent-borne resin prior to curing and in the composite materials, in contrast to forming large aggregates of the bioactive proteins which diminish the functionality of the proteases and protein-polymer composite materials. Proteases are optionally dispersed in the protein-polymer composite material such that the proteases are unassociated with other bioactive proteins and/or form relatively small particles of associated proteins. Illustratively, the average particle size of protease particles in the protein-polymer composite material is less than 10 μm (average diameter) such as in the range of 1 nm to 10 inclusive.

Curable protein-polymer compositions are optionally two-component solvent-borne (2K SB) compositions. Optionally, one component systems (1K) are similarly operable. Illustratively, a protease is entrapped in a coating material such as a latex or enamel paint, varnish, polyurethane gels, or other coating materials. Illustrative examples of incorporating enzymes into paints are presented in U.S. Pat. No. 5,998,200, the contents of which are incorporated herein by reference.

In two-component systems the two components are optionally mixed shortly before use, for instance, application of the curable protein-polymer composition to a substrate to form a protease containing coating such as a bioactive clear coat. Generally described, the first component contains a crosslinkable polymer resin and the second component contains a crosslinker. Thus, the emulsion is a first component containing a crosslinkable resin and the crosslinker is a second component, mixed together to produce the curable protein-polymer composition.

A polymer resin included in methods and compositions of the present invention can be any film-forming polymer useful in coating or substrate compositions, illustratively clear coat compositions. Such polymers illustratively include, aminoplasts, melamine formaldehydes, carbamates, polyurethanes, polyacrylates, epoxies, polycarbonates, alkyds, vinyls, polyamides, polyolefins, phenolic resins, polyesters, polysiloxanes; and combinations of any of these or other polymers.

In particular embodiments, a polymer resin is crosslinkable. Illustratively, a crosslinkable polymer has a functional group characteristic of a crosslinkable polymer. Examples of such functional groups illustratively include acetoacetate, acid, amine, carboxyl, epoxy, hydroxyl, isocyanate, silane, vinyl, other operable functional groups, and combinations thereof.

Examples of organic crosslinkable polymer resins includes aminoplasts, melamine formaldehydes, carbamates, polyurethanes, polyacrylates, epoxies, polycarbonates, alkyds, vinyls, polyamides, polyolefins, phenolic resins, polyesters, polysiloxanes, or combinations thereof.

A cross linking agent is optionally included in the composition. The particular crosslinker selected depends on the particular polymer resin used. Non-limiting examples of crosslinkers include compounds having functional groups such as isocyanate functional groups, epoxy functional groups, aldehyde functional groups, and acid functionality.

In particular embodiments of protein-polyurethane composite materials, a polymer resin is a hydroxyl-functional acrylic polymer and the crosslinker is a polyisocyanate.

A polyisocyanate, optionally a diisocyanate, is a crosslinker reacted with the hydroxyl-functional acrylic polymer according to embodiments of the present invention. Aliphatic polyisocyanates are preferred polyisocyanates used in processes for making protein-polymer composite materials for clearcoat applications such as in automotive clearcoat applications. Non-limiting examples of aliphatic polyisocyanates include 1,4-butylene diisocyanate, 1,4-cyclohexane diisocyanate, 1,2-diisocyanatopropane, 1,3-diisocyanatopropane, ethylene diisocyanate, lysine diisocyanate, 1,4-methylene bis(cyclohexyl isocyanate), diphenylmethane 4,4'-diisocyanate, an isocyanurate of diphenylmethane 4,4'- diisocyanate, methylenebis-4,4'-isocyanatocyclohexane, 1,6-hexamethylene diisocyanate, an isocyanurate of 1,6-hexamethylene diisocyanate, isophorone diisocyanate, an isocyanurate of isophorone diisocyanate, p-phenylene diisocyanate, toluene diisocyanate, an isocyanurate of toluene diisocyanate, triphenylmethane 4,4',4"-triisocyanate, tetramethyl xylene diisocyanate, and meta-xylene diisocyanate.

Curing modalities are those typically used for conventional curable polymer compositions.

Protease-polymer composite materials used in embodiments of the present invention are optionally thermoset protein-polymer composite materials. For example, a substrate or coating material is optionally cured by thermal curing. A thermal polymerization initiator is optionally included in a curable composition. Thermal polymerization initiators illustratively include free radical initiators such as organic peroxides and azo compounds. Examples of organic peroxide thermal initiators illustratively include benzoyl peroxide, dicumylperoxide, and lauryl peroxide. An exemplary azo compound thermal initiator is 2,2'-azobisisobutyronitrile.

Conventional curing temperatures and curing times can be used in processes according to embodiments of the present invention. For example, the curing time at specific temperatures, or under particular curing conditions, is determined by the criteria that the cross-linker functional groups are reduced to less than 5% of the total present before curing. Cross-linker functional groups can be quantitatively characterized by FT-IR or other suitable method. For example, the curing time at specific temperatures, or under particular curing conditions, for a polyurethane protein-polymer composite of the present invention can be determined by the criteria that the cross-linker functional group NCO is reduced to less than 5% of the total present before curing. The NCO group can be quantitatively characterized by FT-IR. Additional methods for assessing the extent of curing for particular resins are well-known in the art. Illustratively, curing may include evaporation of a solvent or by exposure to actinic radiation, such as ultraviolet, electron beam, microwave, visible, infrared, or gamma radiation.

One or more additives are optionally included for modifying the properties of the protease-polymer composite material and/or the admixture of organic solvent and polymer resin, the aqueous lipase solution, the emulsion, and/or the curable composition. Illustrative examples of such additives include a UV absorbing agent, a plasticizer, a wetting agent, a preservative, a surfactant, a lubricant, a pigment, a filler, and an additive to increase sag resistance.

A substrate or coating including a protease is illustratively an admixture of a polymer resin, a surfactant and a non-aqueous organic solvent, mixed to produce an emulsion. The term "surfactant" refers to a surface active agent that reduces the surface tension of a liquid in which it is dissolved, or that reduces interfacial tension between two liquids or between a liquid and a solid.

Surfactants used can be of any variety including amphoteric, silicone-based, fluorosurfactants, anionic, cationic and nonionic such as described in K. R. Lange, Surfactants: A Practical Handbook, Hanser Gardner Publications, 1999; and R. M. Hill, Silicone Surfactants, CRC Press, 1999, incorporated herein by reference. Examples of anionic surfactants illustratively include alkyl sulfonates, alkylaryl sulfonates, alkyl sulfates, alkyl and alkylaryl disulfonates, sulfonated fatty acids, sulfates of hydroxyalkanols, sulfosuccinic acid esters, sulfates and sulfonates of polyethoxylated alkanols and alkylphenols. Examples of cationic surfactants include quaternary surfactants and amineoxides. Examples of nonionic surfactants include alkoxylates, alkanolamides, fatty acid esters of sorbitol or manitol, and alkyl glucamides. Examples of silicone-based surfactants include siloxane polyoxyalkylene copolymers.

In some embodiments, a coating is formed of materials that produce a liquid bioactive coating material suitable for use as a cleaning fluid, illustratively a windshield washer fluid. The inventors surprisingly discovered that inclusion of the active extracellular fragment of enzyme G. stearothermophilus TLP at an activity in excess of 20,000 U/g in a coating material provides unexpectedly superior insect biological stain removal relative to other enzymes, and particularly other proteases. A coating material is optionally a cleaning fluid. Illustrative examples of a cleaning fluid include those described in: U.S. Pat. Nos. 6,881,711; and 6,635,188; the contents of which are incorporated herein by reference. Illustrative examples of fluids for use as a coating material include those sold as BUGWASH by Prestone Products, Corp., XTREME BLUE by Camco Mfg, Inc., Greenboro, N.C., and RAIN X Delcer, from ITW Global Brands, Houston, Tex.

While any commercially available windshield washer fluid can be used as a cleaning fluid for addition of a protease, the inventors surprisingly discovered that coating materials that are low in alcohol content (e.g. less than 0.8%) and have a pH in excess of 5.0, optionally in excess of 8.0, optionally between 5.0 and 12.0, or any value or range therebetween, possess far superior protease activity stability. Optionally, a pH is between 10.0 and 11.0. The pH activity and stability data are surprising for the additional reasons that it is known in the art that the active extracellular fragment of enzyme G. stearothermophilus TLP has an optimal activity at about pH 7.6 with rapidly decreasing activity at higher pH levels. For example, the activity in Britton-Robinson buffer is less than 20% peak activity at a pH at or above 10.0. Additionally, stability falls of significantly at a pH above 5. The combined high activity and stability of the active extracellular fragment of enzyme G. stearothermophilus TLP at relatively high pH values such as above 5.0, optionally above 8.0, particularly above 10.0, more particularly between 10.0 and 11.0, creates an unexpectedly cleaning coating material relative to coating materials combined with other proteases.

In some embodiments, a liquid bioactive coating material includes a surfactant, an ammonia compound, an alcohol, and water. Water is optionally a predominant. A surfactant in such embodiments is illustratively a nonionic surfactants, anionic surfactants, cationic surfactants, zwitterionic surfactants, and mixtures thereof, with specific examples of surfactants being octylphenol ethoxylates, alkyl polyglycosides, sodium alkyl sulfates, and mixtures thereof. A surfactant is optionally present in an amount at or between 0.001% to about 0.25% (by weight). An ammonia compound is illustratively ammonium carbamate, ammonium carbonate, ammonium bicarbonate, ammonium hydroxide, ammonium acetate, ammonium borate, ammonium phosphate, an alkanolamine having 1 to 6 carbon atoms, and ammonia, or combinations thereof. An ammonia compound is optionally present at or between 0.005% to about 1.0% (by weight of $NH_3$). An alcohol is illustratively one or more: water miscible alcohols having 1 to 6 carbon atoms, water miscible glycols and glycol ethers having 2 to 15 carbon atoms and mixtures thereof. Preferred alcohols include methanol, ethanol, isopropanol, propanol, butanol, furfuryl alcohol, tetrahydrofurfuryl alcohol ("THFA") and 1-amino-2-propanol. Preferred glycols and glycol ethers include ethylene glycol, propylene glycol, 2-butoxyethanol sold as BUTYL CELLOSOLVE®, 2-methoxyethanol, 1-methoxy-2-propanol, ethylene glycol dimethyl ether, 1,2-dimethoxypropane, 2-(2-propoxyethoxy)ethanol, 2-[2-(2-propoxyethoxy)ethoxy]ethanol, 2-(2-isopropoxyethoxy)ethanol, 2-[2-(2 isopropoxyethoxy)ethoxy]ethanol, 2-(2-butoxyethoxy)ethanol, 2-[2-(2-butoxyethoxy)ethoxy]ethanol, 2-(2-isobutoxyethoxy)ethanol, 2-[2-(2 isobutoxyethoxy)ethoxy]ethanol, 2-(2-propoxypropoxy)-propan-1-ol, 2-[2-(2-propoxypropoxy)propoxy]propan-1-ol, 2-(2-isopropoxypropoxy)-propan-1-ol, 2-[2(2-isopropoxypropoxy)propoxy]propan-1-ol, 2-(2-butoxypropoxy)-propan-1-ol, 2-[2 (2-butoxypropoxy)propoxy]propan-1-ol, 2-(2-isobutoxypropoxy)-propan-1-ol and 2[2-(2-isobutoxypropoxy)propoxy]propan-1-ol. Preferably, ethanol, isopropanol, 2-butoxyethanol or 1-amino-2-propanol methanol, ethanol, isopropanol, propanol, butanol, furfuryl alcohol, tetrahydrofurfuryl alcohol, 1-amino-2-propanol, ethylene glycol, propylene glycol, and 2-butoxyethanol, or combinations thereof are used.

A liquid bioactive coating material is optionally formed by combining a coating material with one or more proteases such that the protease is in solution or suspension. A protease containing coating material is optionally mixed such as by vortex mixing until a solution of protease is achieved. The amount of protease is illustratively 0.1 to 50 mg in ~4 l coating material.

When a surface, which is optionally a substrate or a coated substrate, is contacted with biological material to produce a biological stain, the protease enzyme or combinations of enzymes in a coating material are placed in contact with the stain, or components thereof. The contacting allows the enzymatic activity of the protease to interact with and enzymatically alter the components of the stain improving its removal from the substrate or coating.

Enzyme containing substrates or coatings have a surface activity generally expressed in Units/cm$^2$. Substrates and coatings optionally have functional surface activities of greater than 0.0075 Units/cm$^2$. In some embodiments surface activity is between 0.0075 Units/cm$^2$ and 0.05 Units/cm$^2$ inclusive. Optionally, surface activity is between 0.0075 Units/cm$^2$ and 0.1 Units/cm$^2$ inclusive. Optionally, surface activity is between 0.01 Units/cm$^2$ and 0.05 Units/cm$^2$ inclusive.

It is appreciated that the inventive methods of facilitating stain removal will function at any temperature whereby the protease is active. Optionally, the inventive process is performed at 4° C. Optionally, an inventive process is performed at 25° C. Optionally, an inventive process is performed at ambient temperature. It is appreciated that the inventive process is optionally performed from 4° C. to 125° C., or any single temperature or range therein.

The presence of protease combined with the material of a substrate or a coating, optionally, with water or other fluidic rinsing agent, breaks down stains for facilitated removal.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002.

Various aspects of the present invention are illustrated by the following non-limiting examples. The examples are for illustrative purposes and are not a limitation on any practice of the present invention. It will be understood that variations and modifications can be made without departing from the spirit and scope of the invention.

Example 1

Production of a bacterial neutral protease from *Bacillus stearothermophilus* containing material operable for coating a substrate.

Materials: Freeze-dried crickets are purchased from PetSmart. Cricket bodies reportedly contain 58.3% protein. (D. Wang, et al., *Entomologic Sinica,* 2004; 11:275-283, incorporated herein by reference.) α-Amylase, Lipase PS, Protease N, Protease A, Protin SD AY-10, active extracellular fragment of *G. stearothermophilus* TLP (THERMOASE C160), and THERMOASE GL30 (low activity preparation of *B. stearothermophilus* TLP) are obtained from AMANO Enzyme Inc. (Nagoya, JAPAN). Polyacrylate resin Desmophen A870 BA, and the hexamethylene diisocyanate (HDI) based polyfunctional aliphatic polyisocyanate resin Desmodur N 3600 are obtained from Bayer Corp. (Pittsburgh, Pa.). The surfactant BYK-333 is obtained from BYK-Chemie (Wallingford, Conn.). 1-butanol and 1-butyl acetate are obtained from Sigma-Aldrich Co. (Missouri, USA). Aluminum paint testing panels are purchased from Q-Lab Co. (Cleveland, USA). All other reagents involved in the experiments are of analytical grade.

Enzyme based 2K SB PU coatings are prepared by either a draw-down method or by spray application and used for subsequent biological stain removal experiments. Each enzyme is dissolved in DI water to a final enzyme solution concentration of 200 mg/mL for all water borne (WB) coatings. For solvent borne (SB) enzyme prepared coatings 50 mg/mL enzyme is used. A solution of 150 ml of deionized water containing 1.5 g of the active extracellular fragment of enzyme *G. stearothermophilus* TLP is first purified by ultrafiltration (molecular weight cut-off of 30 kDa, all liquids were kept on ice).

For the draw-down method or coating preparation, the surfactant BYK 333 is diluted with 1-butanol to the concentration of 17% by weight. The resin part of the 2K SB PU coating is prepared by mixing 2.1 g of Desmophen A 870 with 0.5 mL of 1-butyl acetate and 0.1 mL surfactant in a 20 mL glass vial. The solution is mixed using a microspatula for 1 min followed by addition of 0.6 mL of enzyme solution (or DI water for control coating without enzyme) followed by mixing for another 1 min. This solution is then poured out into a 20-mL glass vial with 0.8 g of NA 3600 and stirred for 1 min. This formulation produces an enzyme concentration of 6% by weight. Pre-cleaned aluminum testing panels are coated with the enzyme containing coating material using a draw-down applicator with a wet film thickness of 2 mils. The coating panels are baked at 80° C. for 30 minutes and then cured at ambient temperature for 7 days.

For the spray application method, coating are prepared essentially as described in FIG. 1.

A cleaning fluid as a coating material including the active extracellular fragment of enzyme *G. stearothermophilus* TLP is produced by intermixing the TLP at 0.1 mg to 20 mg/liter of the cleaning fluid in a mixing vessel at room temperature at least one hour prior to use. The cleaning fluid is formed from 1-amino-2-propanol (0.2% w/w), 4-(1,1,3,3-Tetramethylbutyl)phenyl-polyethylene glycol t-Octylphenoxypolyethoxyethanol Polyethylene glycol tert-octylphenyl ether (TRITON X-100) (0.04% w/w), ammonia (0.084% w/w; from 28% $NH_3$ in water); with the balance water. All of the components of the cleaning fluid are obtained commercially as follows: TRITON X-100 from Union Carbide/Dow Chemical; ammonia and 1-amino-2propanol from Sigma-Aldrich Chemical Company Inc.; and active extracellular fragment of *Geobacillus stearothermophilus* TLP (THERMOASE C160) from Amano Enzyme, Inc. A cleaning fluid is mixed with the active extracellular fragment *G. stearothermophilus* TLP by agitation or by vortex mixing. The resulting *G. stearothermophilus* TLP containing cleaning fluid is stored at ambient temperature.

Example 2

Figure 2:
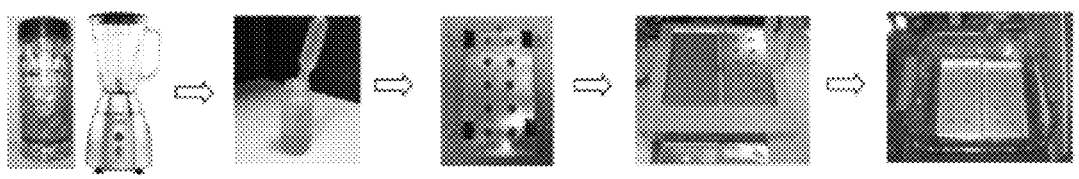
FIG. 2 represents a schematic of stain application and protease mediated stain removal on a coated substrate.

Preparation of biological stains and application to a coated substrate. An exemplary schematic of an experimental procedure is provided in FIG. 2. 60 g of Freeze-dried crickets are chopped into powder by a blender (Oster, 600 watt) for 10 min. The stain solution is prepared by vigorously mixing 2 g of cricket powder with 6 mL of DI water. A template of uniform spacing is used to apply the stain on the coating surface. The cricket stains are dried at 40° C. for 5 min followed by placing the coating panels into a glass dish and rinsing with 200 mL of DI water under 300 rpm shaking at RT for various times. The time of the stain removal is recorded. In order to reduce random error, the time of the first and last drop removed are not included. The average rinsing time of eight stain spots is averaged for stain removal time.

Example 3

Drying time affects stain removal time. Stained coated substrate panels prepared with coatings as in Example 1 and insect stains as in Example 2 are subjected to drying at 40° C. for various times. The rinsing time of stain drops strongly depends on the drying time. The control protease free coating, after being dried for 5 min, produces firmly adhered stain drops that are not removed by rinsing for 3 hr (Table 1).

TABLE 1

| | Drying Time (min) | | |
|---|---|---|---|
| | 3 | 3.2 | 5 |
| Average washing time (min) | 2.8 | 4.9 | >180 |

For the active extracellular fragment of enzyme *G. stearothermophilus* TLP containing coated panes, the rinsing time increases with longer drying time yet at equivalent drying times relative to control the protease containing coating promotes dramatically improved stain removal. (Table 2).

TABLE 2

| | Drying Time (min) | |
|---|---|---|
| | 5 | 10 |
| Average washing time (min) | 28.7 | 79.3 |

Example 4

Increased rinsing intensity reduces stain removal time. The panels prepared as in Examples 1 and 2 are subjected to various rinsing intensities. Reduced rinsing time is achieved by increasing rinsing intensity for the active extracellular fragment of enzyme *G. stearothermophilus* TLP containing coatings on substrates (Table 3).

TABLE 3

| | Shaking speed (rpm) | | |
|---|---|---|---|
| | 200 | 250 | 300 |
| Average washing time (min) | 56.5 | 44.4 | 28.7 |

Example 5

Coatings containing various enzymes are prepared as in Example 1. Each coating is analyzed for performance by measurement of average rinsing time using a standard protocol of applying a cricket stain to a coated substrate, drying for 5 min at 40° C. and rinsing in water or in protease containing cleaning fluid at an intensity of 300 RPM. For removal of insect stains by a TLP containing cleaning fluid, the fluid is prepared as described in Example 1. Insect material is applied onto a glass substrate dried on a heating plate at 60° C. for a period. After drying, drops of 50 µl enzyme containing cleaning fluids of Example 1 are added onto dry stain spots via a multi-channel pipette, followed by an incubation for 10 minutes at ambient temperature. The identical volume of control (protease free) washer fluids are added onto the control spots on the same substrate. The substrate is then immersed face-up into a deionized water bath while horizontally shaking at 100 rpm. The stain spots retained on the coatings after a desired shaking time are counted during the washing for quantitative analysis. The control and various protease containing coatings are also evaluated for roughness, contact angle, and gloss. The results are depicted in Table 4.

TABLE 4

| Coatings | Average Washing time | Roughness (µm) | Contact Angle | Gloss (60°) |
|---|---|---|---|---|
| SB control coating | >3 hr | 0.053 | 76.2 | 163.0 |
| Lipase PS based SB coating | >3 hr | 0.063 | 88.0 | 147.9 |
| α-Amylase based SB coating | >3 hr | 0.078 | 80.5 | 148.4 |
| Thermoase C160 based SB coating | 28 min | 0.078 | 86.4 | 148.4 |

The active extracellular fragment of enzyme *G. stearothermophilus* TLP based coatings as well as other TLP containing cleaning fluids have an improved self-cleaning function against insect body stains compared with other coating materials containing either no enzyme or alternative enzymes (no enzyme, Lipase PS, and α-amylase). In addition, the coating surface properties are insignificant different between the active extracellular fragment of enzyme *G. stearothermophilus* TLP based coating and the control, Lipase PS, or α-amylase based coatings. These results indicate that physical characteristics of the coatings are not differentially affecting the coating performance.

Figure 3:
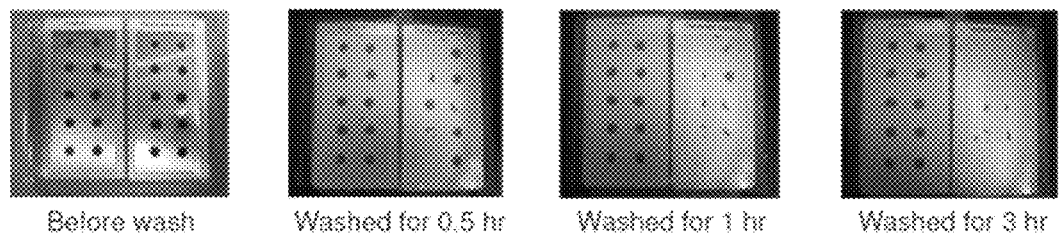
FIG. 3 illustrates improved rinsing of insect stains using the active extracellular fragment of enzyme *G. stearothermophilus* TLP (THERMOASE C160) based coating relative to an enzyme free control.

The rinsing times of each enzyme containing coating is compared. FIG. 3 demonstrates comparison of a control SB coating (enzyme free, left panel) with an active extracellular fragment of enzyme *G. stearothermophilus* TLP based coating (right panel). After 30 minutes of rinsing the active extracellular fragment of enzyme *G. stearothermophilus* TLP based coating shows significant stain removal. The control shows no significant stain removal out to 3 hours of rinsing.

Figure 4:
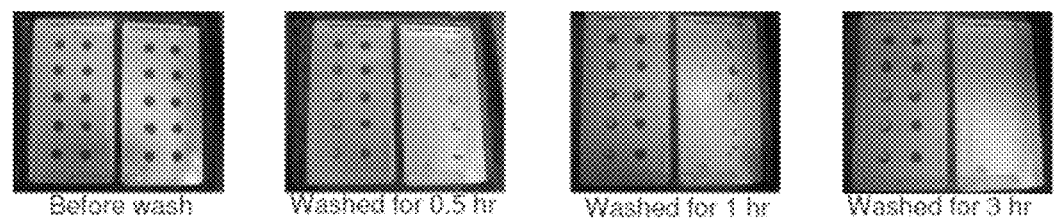
FIG. 4 illustrates improved rinsing of insect stains using the active extracellular fragment of enzyme *G. stearothermophilus* TLP (THERMOASE C160) based coating relative to a Lipase PS based coating.
Figure 5:
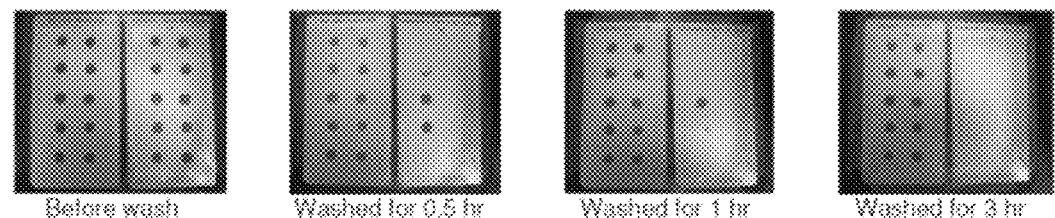
FIG. 5 illustrates improved rinsing of insect stains using the active extracellular fragment of enzyme *G. stearothermophilus* TLP (Thermoase C160) based coating relative to an α-Amylase based coating.

Similar results are observed comparing an active extracellular fragment of enzyme *G. stearothermophilus* TLP based coating with a lipase and α-amylase based coating. In FIGS. 4 and 5 respectively, lipase and α-amylase (left panels) show significant adherence of insect stains remaining for the entire three hour rinsing period. In contrast the active extracellular fragment of enzyme G. stearothermophilus TLP based coatings show dramatic stain removal after an initial 30 min rinsing period with essentially complete stain removal by three hours.

Figure 14:
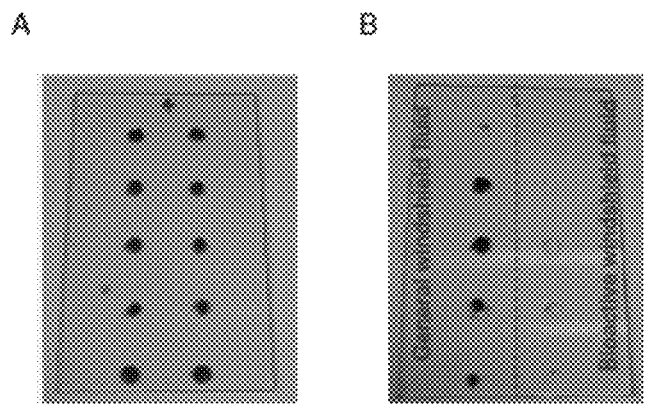
FIG. 14 illustrates the ability of a coating of windshield washer fluid alone (A) or a coating of windshield washer fluid containing the active extracellular fragment of enzyme *G. stearothermophilus* TLP and its ability to remove insect material from a glass substrate.

Similarly excellent results are observed for cleaning fluids containing active extracellular fragment of enzyme G. stearothermophilus TLP. FIG. 14 demonstrates a comparison of the cleaning fluid of Example 1 with or without the active extracellular fragment of enzyme G. stearothermophilus TLP with (A) representing glass substrate with insect stains before rinsing, and (B) after rinsing. The cleaning fluid including the active extracellular fragment of enzyme G. stearothermophilus TLP is far superior in promoting insect stain removal from a glass substrate than the same fluid in the absence of the enzyme.

Example 6

Figure 6:
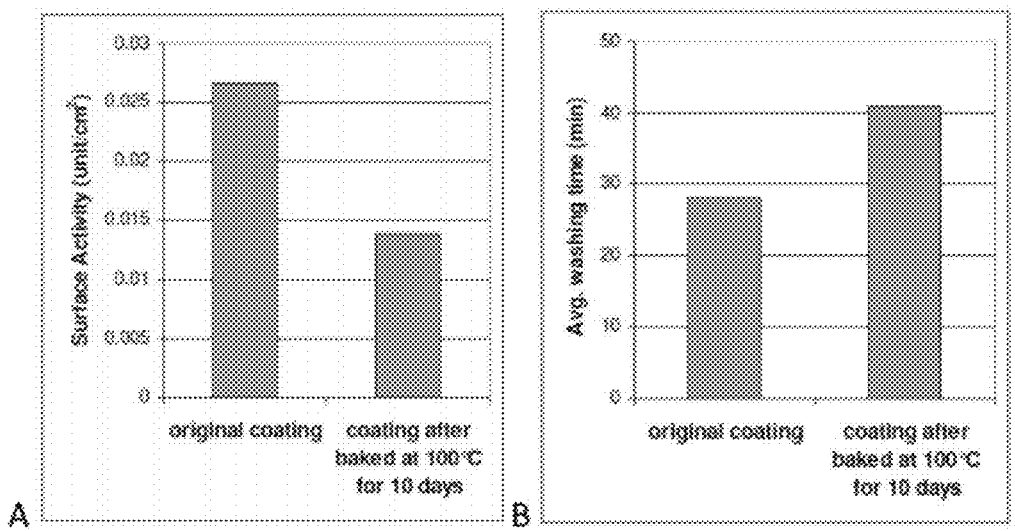
FIG. 6 illustrates affects on 100° C. baking for 10 days on surface enzyme activity (A) and stain cleaning time (B)
Figure 7:
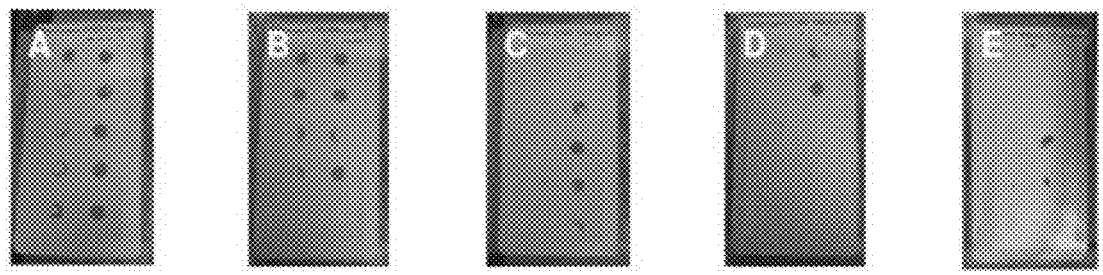
FIG. 7 illustrates increased loading of protease increases self-cleaning performance with relative enzyme loading concentrations of 0.2% (A), 2.0% (B), 4.0% (C), 6.0% (D), and 8.0% (E)

Affect of surface heating on protease function. Panels coated with the active extracellular fragment of enzyme G. stearothermophilus TLP based coatings as in Example 1 are subjected to baking temperatures of 100° C. for 10 days followed by determination of change in surface enzyme activity. Proteolytic surface activity of protease containing coatings is determined following the method of Folin and Ciocalteau, J. Biol. Chem., 1927; 73: 627-50, incorporated herein by reference. Briefly, 1 mL of 2% (w/v) casein in sodium phosphate (0.05 M; pH 7.5) buffer solution is used as substrate together with 200 µl of sodium acetate, 5 mM calcium acetate (10 mM; pH 7.5). The substrate solution is pre-incubated in a water bath for 3 min to reach 37° C. The reaction is started by adding one piece of sample plate coated with the active extracellular fragment of enzyme G. stearothermophilus TLP based coating (1.2×1.9 cm$^2$) followed by shaking for 10 min at 200 rpm at which time the reaction is stopped by adding 1 ml of 110 mM tricholoroacetic acid (TCA) solution. The mixture is incubated for 30 min at 37° C. prior to centrifugation. The equivalent of tyrosine in 400 µL of the TCA-soluble fraction is determined at 660 nm using 200 µL of 25% (v/v) Folin-Ciocalteau reagent and 1 mL 0.5 M sodium carbonate. One unit of activity is defined as the amount of enzyme hydrolyzing casein to produce absorbance equivalent to 1.0 µmmol of tyrosine per minute at 37° C. This result is converted to Units/cm$^2$. FIG. 6 illustrates that the active extracellular fragment of enzyme G. stearothermophilus TLP surface activity is reduced by approximately 50% after long term high temperature baking (FIG. 6A). Coincidentally, the time of stain cleaning is increased (FIG. 6B).

Example 7

Enzyme loading is titered in coatings prepared and coated onto substrate panels as in Example 1 and with insect stains applied as in Example 2 at loading concentrations of enzyme of 0.2% (A), 2.0% (B), 4.0% (C), 6.0% (D), and 8.0% (E) active extracellular fragment of enzyme G. stearothermophilus TLP, and the thermolysin-like-proteins from Bacillis cereus, Lactobacillis sp., Bacillis megaterium, Alicyclobacillis acidocaldarious, Bacillis caldolyticus, Bacillis thermoproteolyticus, Bacillus stearothermophilus, Bacillus subtilis, Bacillus amyloliquefaciens), and Lysteria monocytogenes. The panels are baked for 5 min at 40° C. and washed at 300 RPM for three hours. Increased protease loading correlates with increased rinsing performance (FIG. 7A-E depicting results for the active extracellular fragment of enzyme G. stearothermophilus TLP).

Example 8

Figure 8:
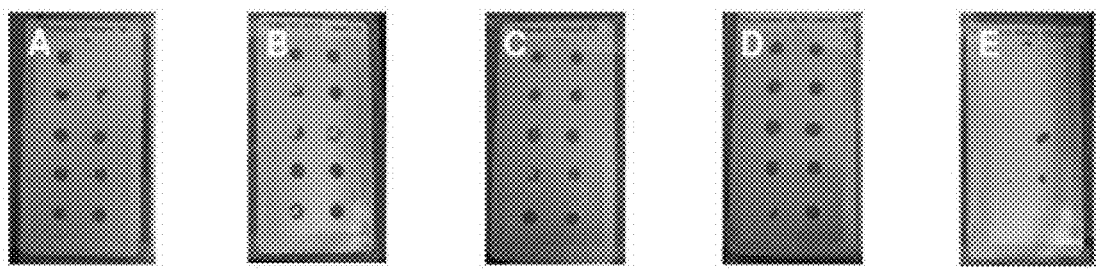
FIG. 8 illustrates rinsing of insect stains by a (A) Protease N based SB coating, (B) Protin SD AY-10 based SB coating, (C) Protease A based SB coating, (D) THERMOASE GL30 based SB coating (<0.0075 units/cm² surface *B. stearothermophilus* TLP), or (E) active extracellular fragment of *G. stearothermophilus* TLP (THERMOASE C160) based SB coating.

Comparison of various protease types on insect stain removal. Coatings are prepared as in Example 1 using protease N (bacillolysin) as a putative cysteine protease, Protin SD AY10 (subtilisin from Bacillus licheniformis) as a putative serine protease, protease A as an exemplary metalloprotease, and the active extracellular fragment of enzyme G. stearothermophilus TLP and thermolysin-like-proteins of Example 7, and coated onto substrates as in Example 1 with insect staining as in Example 2. The different enzyme containing coatings are compared after baking for 5 min at 40° C. and rinsing at 300 RPM for 3 hours. Surprisingly, only the active extracellular fragment of enzyme G. stearothermophilus TLP based coatings show the dramatically improved self-cleaning function which is not observed by coatings including, a serine protease, a cysteine protease, or another metalloprotease. (Table 5 and FIG. 8.)

TABLE 5

| Protease in Coatings | Protease Group | Washing time | Activity (KU/g) |
|---|---|---|---|
| Bacillolysin | Cyserine protease | >3 hr | 150 |
| Subtilisin | Serine protease | >3 hr | 90 |
| Oryzin | Metalloprotease | >3 hr | 20 |
| TLP | Metalloprotease | >3 hr | 300 |
| Sterolysin | Metalloprotease | 28 min | 1600 |

Example 9

Figure 9:
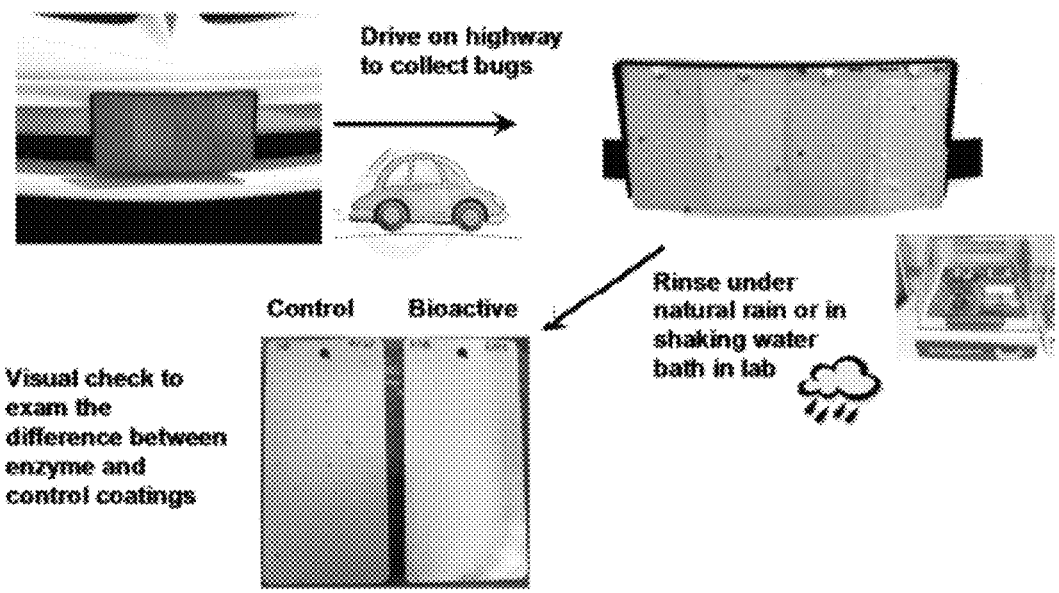
FIG. 9 illustrates a schematic of a road test protocol for active stain removal by an embodiment of a coating.

Test panels are prepared as in Example 1 and are mounted onto the front bumpers of test vehicles. A schematic of a road-test protocol is illustrated in FIG. 9. Real-life insects are collected from the road by driving. The vehicle is driven during summer evenings for ~500 miles to collect insect bodies. The average speed of driving is 65 mph.

Within three days of insect collection the panels are rinsed either in natural rain (driving condition) or in lab on a water bath at a rate of shaking rate of 200 rpm. Photos are taken prior to and after the rinsing procedure. Panels are visually checked and counted prior to, during, and after rinsing to identify differences in stain removal from test and control panels.

Figure 10:
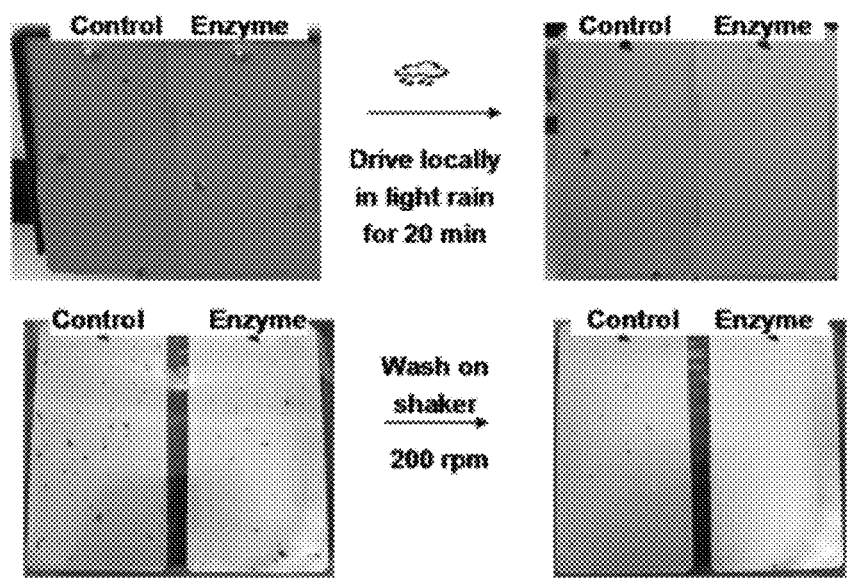
FIG. 10 illustrates rain or water bath rinsing of enzyme containing or control coatings after depositing insect bodies during road driving.
Figure 11:
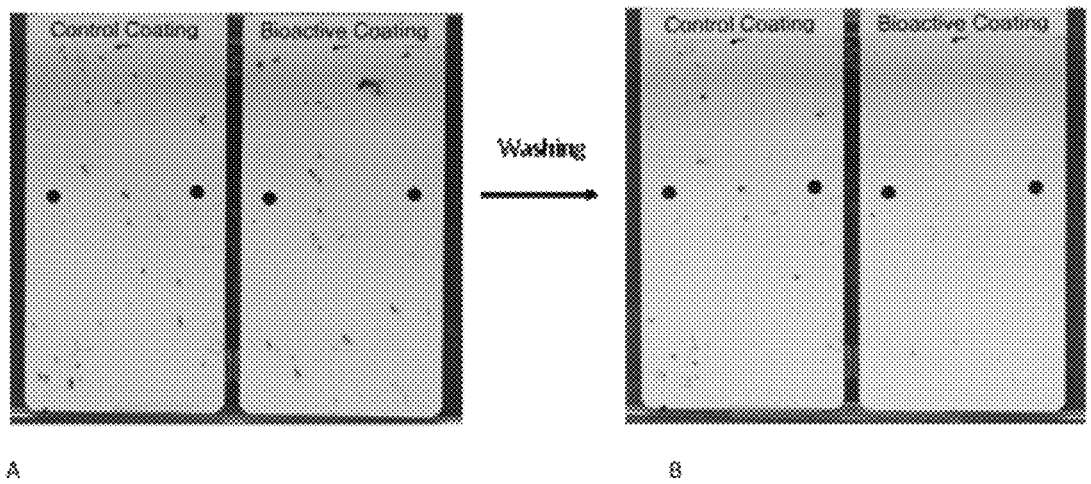
FIG. 11 illustrates rain or water bath rinsing of enzyme containing or control coatings after depositing insect bodies during road driving, WBS represents enzyme coatings; WBB represents control coatings; (A) panes are before rinsing, (B) 2 hours of rinsing; diamonds represent control coatings and X represents bioactive coating.
Figure 12:
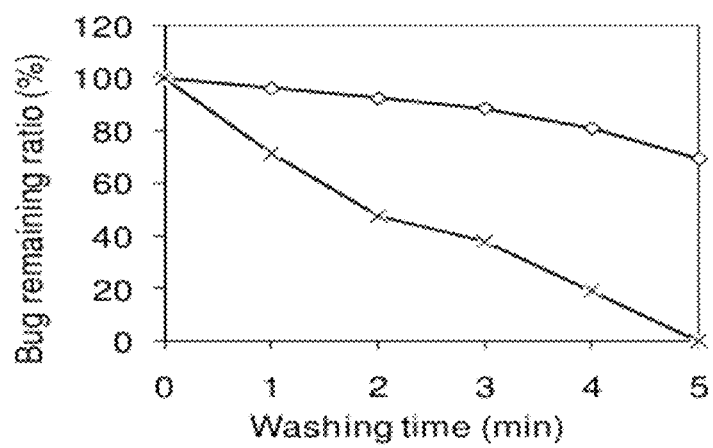
FIG. 12 illustrates average road obtained insect stain removal from panels coated with an enzyme containing coating or a control coating.

A clear increase in stain-removal effectiveness under mild rinsing is observed on enzyme-containing coatings relative to control coatings without enzyme as is illustrated in FIGS. 10 and 11. The road test is repeated three times and the average percent remaining insect stains in enzyme containing and control coatings after rinsing for various times are plotted in FIG. 12. The enzyme containing coatings promote active insect stain removal using environmentally obtained insects under normal road driving conditions.

Example 10

Figure 13:
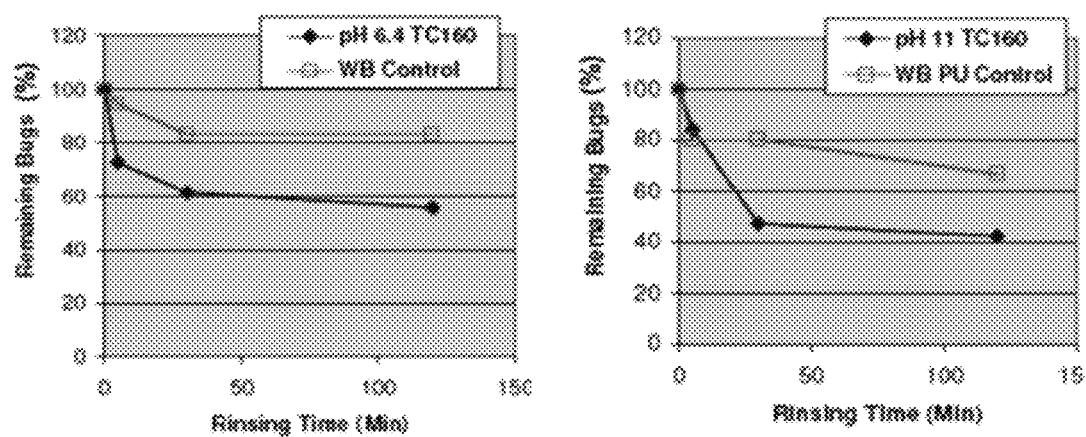
FIG. 13 illustrates average road obtained insect stain removal from panels coated with an enzyme containing coating or a control coating whereby the enzyme containing coatings are prepared at different buffer pH levels.

Enzyme containing coatings are prepared as in Example 1 using buffers of pH 6.4 and pH 11. Coated aluminum plates are subjected to insect staining as in Example 9. Enzyme containing coatings prepared at both pH levels are superior to control (FIG. 13).

Example 11

Figure 15:
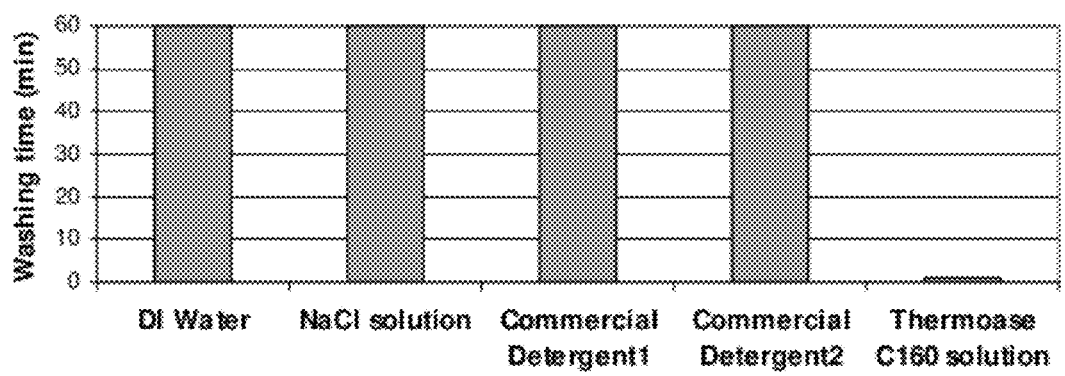
FIG. 15 illustrates that the presence of the active extracellular fragment of enzyme *G. stearothermophilus* TLP effectively promotes insect stain removal relative to traditional water and commercial windshield washer fluids.

Various cleaning fluids are analyzed for performance by measurement of average rinsing time using a standard protocol. For removal of insect stains by an active extracellular fragment of active extracellular fragment of enzyme *G. stearothermophilus* TLP containing cleaning fluid, the fluid is prepared as described in Example 1. Control cleaning fluids of Rain-X Bug Pre-wash Gel (Commercial Detergent 1), Rain-X Foaming Car Wash (Commercial Detergent 2), a sodium chloride solution, and water alone are compared. Insect material is applied onto a glass substrate dried on a heating plate at 60° C. for a period. After drying, drops of 50 μl enzyme containing cleaning fluids of Example 1 are added onto dry stain spots via a multi-channel pipette, followed by an incubation for 10 minutes at ambient temperature. The identical volume of control (protease free) washer fluids are added onto the control spots on the same substrate. The substrate is then immersed face-up into a deionized water bath while horizontally shaking at 100 rpm. The substrate is agitated for 1 hour and the time of each spot removal is recorded. FIG. 15 illustrates that the water, NaCl, and both commercial detergents leave insect material on the glass substrate for greater than one hour, whereas the active extracellular fragment of enzyme *G. stearothermophilus* TLP containing cleaning fluid removes the insect stain much more quickly.

Figure 16:
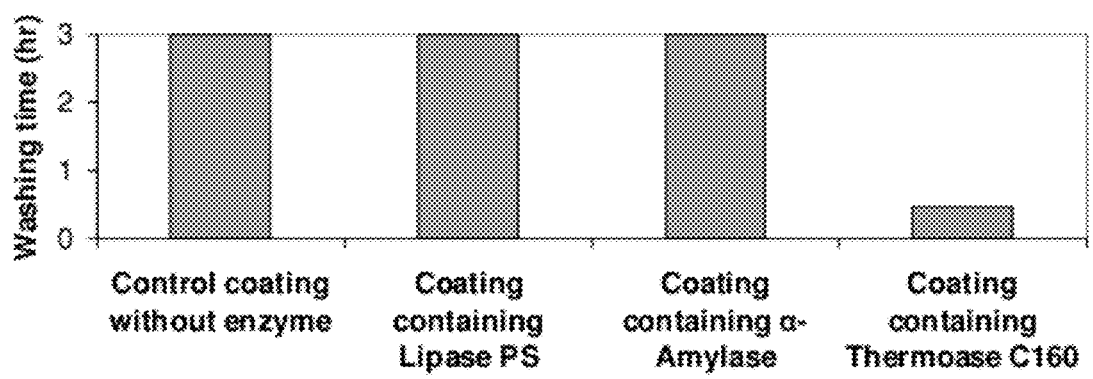
FIG. 16 illustrates that the active extracellular fragment of enzyme *G. stearothermophilus* TLP surprisingly and specifically is far superior to other expected enzymes in a coating material at removing insect stains.

Similar experiments are performed using cleaning fluids prepared as in Example 1 with substitution of lipase (LIPASE PS), α-amylase, or active extracellular fragment of *G. stearothermophilus* TLP (THERMOASE C160), or no enzyme. The experiments above are repeated with the exception that shaking in water is continued out to three hours. As illustrated in FIG. 16, the active extracellular fragment of enzyme *G. stearothermophilus* TLP containing cleaning fluid was the only enzyme tested with the ability to remove the insect stain from the glass substrate in the test period indicating that this protease is unique in its ability to promote removal of insect material from a surface.

Example 12

Figure 17:
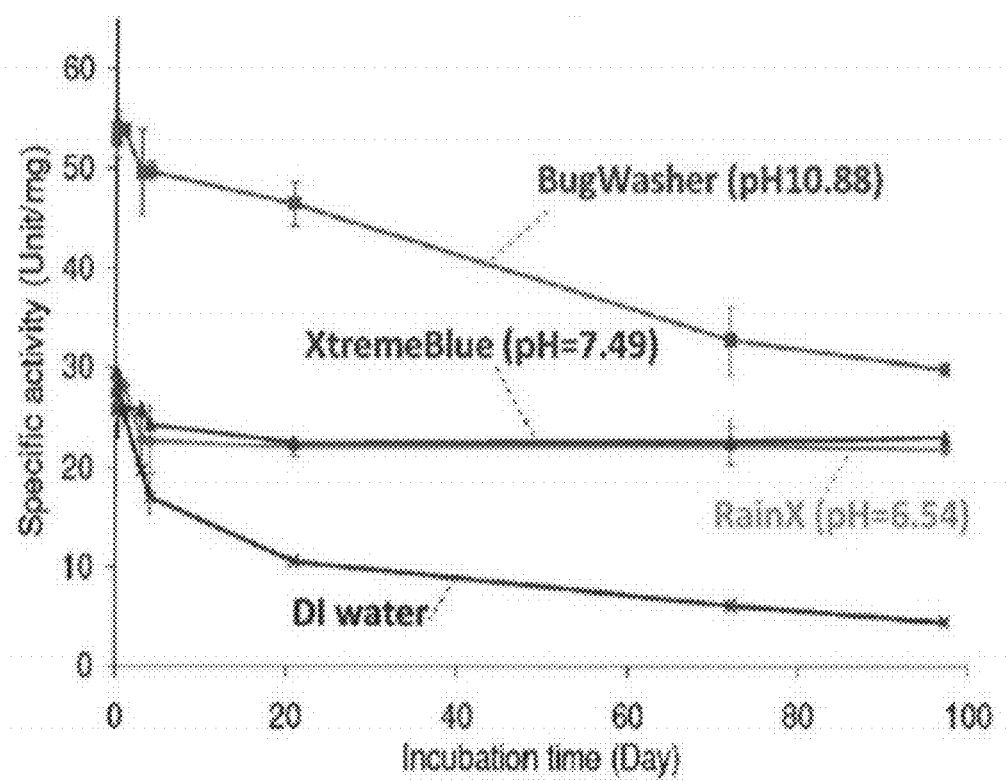
FIG. 17 illustrates the specific activity and stability of the active extracellular fragment of enzyme *G. stearothermophilus* TLP in various cleaning fluids.

A cleaning fluid containing the active extracellular fragment of enzyme *G. stearothermophilus* TLP with high pH demonstrates increased specific activity and excellent stability relative to the active extracellular fragment of enzyme *G. stearothermophilus* TLP containing fluids with lower pH. Various commercial enzyme free cleaning fluids (RAIN-X De Icer; PRESTONE BUG WASH; and EXTRME BLUE) and water are used as a base for the addition of the active extracellular fragment of enzyme *G. stearothermophilus* TLP using the procedure of Example 1. The protease containing cleaning fluids are stored at ambient temperature and assayed at various timepoints using the procedure of Example 11 for their ability to promote insect stain removal. As is illustrated in FIG. 17, the high pH material shows both surprisingly higher specific activity at all time points and excellent stability.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified or synthesized by one of ordinary skill in the art without undue experimentation. Methods of nucleotide amplification, cell transfection, and protein expression and purification are similarly within the level of skill in the art.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A method of facilitating the removal of a biological stain containing a protein component on a substrate or a coating comprising:

providing a liquid coating material;

associating an active extracellular portion of bacterial neutral thermolysin-like protease from *Geobacillus stearothermophilus* with said liquid coating material to form a liquid bioactive coating material at a pH of 10.0 to 11.0, such that said protease is capable of enzymatically degrading a protein component of a biological stain, wherein said protease has a specific activity in excess of 20,000 U/g in said liquid bioactive coating material.

2. The method of claim 1 wherein said protease is in solution in said liquid bioactive coating material.

3. The method of claim 1 wherein said liquid coating material comprises an alcohol, said alcohol present at less than 0.8% by weight.

4. The method of claim 1 wherein said liquid coating material comprises ammonia, or a derivative of ammonia.

5. The method of claim 1 further comprising applying said liquid bioactive coating material to a biological stain on a coating material or substrate, thereby promoting removal of said stain.

6. The method of claim 5 wherein said biological stain is an insect stain.

7. The method of claim 5 wherein said biological stain is present on a substrate.

8. The method of claim 7 wherein said substrate is glass.

9. A liquid bioactive coating material for facilitating removal of a biological stain containing a protein component comprising:

a liquid coating material; and an active extracellular portion of bacterial neutral thermolysin-like protease from *Geobacillus stearothermophilus*, said protease capable of degrading a biological stain containing a protein component wherein said protease is associated with said liquid coating material, wherein the liquid bioactive coating material has a pH of 10.0 to 11.0, wherein said protease has a specific activity in excess of 20,000 U/g in said liquid bioactive coating material.

10. The liquid bioactive coating material of claim 9 wherein said protease is in solution.

11. The liquid bioactive coating material of claim 9 wherein said liquid bioactive coating material comprises an alcohol, said alcohol present at less than 0.8% by weight.

12. The liquid bioactive coating material of claim 9 wherein said liquid bioactive coating material comprises ammonia, or a derivative of ammonia.

* * * * *